(12) United States Patent
Alston et al.

(10) Patent No.: US 7,185,651 B2
(45) Date of Patent: Mar. 6, 2007

(54) FLOW REGULATOR FOR AEROSOL DRUG DELIVERY AND METHODS

(75) Inventors: William Alston, San Jose, CA (US); Stephen Smeulders, Pittsford, NY (US)

(73) Assignee: Nektar Therapeutics, San Carlos, CA (US)

( * ) Notice: Subject to any disclaimer, the term of this patent is extended or adjusted under 35 U.S.C. 154(b) by 426 days.

(21) Appl. No.: 10/257,745

(22) PCT Filed: May 14, 2003

(86) PCT No.: PCT/US02/19388

§ 371 (c)(1),
(2), (4) Date: May 14, 2003

(87) PCT Pub. No.: WO03/000329

PCT Pub. Date: Jan. 3, 2003

(65) Prior Publication Data

US 2004/0000309 A1   Jan. 1, 2004

(51) Int. Cl.
*A62B 9/02* (2006.01)
*A61M 16/00* (2006.01)

(52) U.S. Cl. ............... 128/205.24; 128/203.15; 128/204.26

(58) Field of Classification Search ........... 128/200.14, 128/200.22, 200.23, 203.12, 203.15, 203.21, 128/204.26, 205.24; 137/81.1, 78.5; 251/5, 251/30.02, 30.05
See application file for complete search history.

(56) References Cited

U.S. PATENT DOCUMENTS

| | | | |
|---|---|---|---|
| 2,587,215 A | 2/1952 | Priestly | |
| 3,788,310 A | 1/1974 | Fleischmann | |
| 3,837,341 A | 9/1974 | Bell | |
| 4,086,918 A | 5/1978 | Russo | |
| 4,106,503 A | 8/1978 | Rosenthal et al. | |

(Continued)

FOREIGN PATENT DOCUMENTS

| | | |
|---|---|---|
| EP | 0808635 | 11/1997 |
| EP | 0863343 | 9/1998 |
| EP | 0714314 | 10/1998 |
| EP | 0805696 | 3/2000 |
| GB | 1598053 | 9/1981 |

(Continued)

OTHER PUBLICATIONS

Barrowcliffe et al., "The In-Vitro Evaluation of Novel Multi-Dose Dry Powder Inhaler," CCL Pharmaceuticals Ltd., pp. 82-85.

(Continued)

*Primary Examiner*—Teena K. Mitchell
*Assistant Examiner*—Amadeus Lopez
(74) *Attorney, Agent, or Firm*—Guy V. Tucker (57) ABSTRACT

An aerosolization device comprises a housing having a mouthpiece, and a flow path arrangement in fluid communication with the mouthpiece. The flow path arrangement has a flow regulating valve and a threshold valve, where the threshold valve is configured to open at a first vacuum level and to close at a second vacuum level that is less than the first vacuum level. The housing includes a region that is adapted to hold a powder in fluid communication with the flow path arrangement so that air drawn through the mouthpiece opens the threshold valve once the first vacuum level is exceeded and remains open until the vacuum falls below the second vacuum level. The flow rate of the air drawn through the mouthpiece is regulated by the flow regulating valve to remain within a certain range while the threshold valve remains open.

22 Claims, 4 Drawing Sheets

U.S. PATENT DOCUMENTS

| | | |
|---|---|---|
| 4,114,608 A | 9/1978 | Russo |
| 4,170,228 A | 10/1979 | Elson et al. |
| 4,259,951 A | 4/1981 | Chernack et al. |
| 4,274,404 A | 6/1981 | Molzan et al. |
| 4,284,083 A | 8/1981 | Lester |
| 4,338,931 A | 7/1982 | Cavazza |
| 4,391,283 A | 7/1983 | Sharpless et al. |
| 4,442,856 A | 4/1984 | Betz |
| 4,444,202 A | 4/1984 | Rubin et al. |
| 4,484,577 A | 11/1984 | Sackner et al. |
| 4,495,944 A | 1/1985 | Brisson et al. |
| 4,533,137 A | 8/1985 | Sonne |
| 4,558,710 A | 12/1985 | Eichler |
| 4,592,348 A | 6/1986 | Waters, IV et al. |
| 4,627,432 A | 12/1986 | Newell et al. |
| 4,677,975 A | 7/1987 | Edgar et al. |
| 4,778,054 A | 10/1988 | Newell et al. |
| 4,811,731 A | 3/1989 | Newell et al. |
| 4,907,583 A | 3/1990 | Wetterlin et al. |
| 4,926,852 A | 5/1990 | Zoltan et al. |
| 4,955,371 A | 9/1990 | Zamba et al. |
| 4,991,745 A | 2/1991 | Brown |
| 5,027,806 A | 7/1991 | Zoltan et al. |
| 5,033,655 A | 7/1991 | Brown |
| 5,039,280 A * | 8/1991 | Saulgeot et al. ............ 417/205 |
| 5,040,527 A | 8/1991 | Larson et al. |
| 5,042,467 A | 8/1991 | Foley |
| 5,042,472 A | 8/1991 | Bunin |
| 5,069,204 A | 12/1991 | Smith et al. |
| 5,161,524 A | 11/1992 | Evans |
| 5,167,506 A | 12/1992 | Kilis et al. |
| 5,184,641 A | 2/1993 | Kuhn |
| 5,201,308 A | 4/1993 | Newhouse |
| 5,213,236 A | 5/1993 | Brown et al. |
| 5,284,133 A | 2/1994 | Burns et al. |
| 5,301,666 A | 4/1994 | Lerk et al. |
| 5,320,094 A | 6/1994 | Laube et al. |
| 5,333,106 A | 7/1994 | Lanpher et al. |
| 5,339,995 A | 8/1994 | Brown et al. |
| 5,364,838 A | 11/1994 | Rubsamen |
| 5,377,877 A | 1/1995 | Brown et al. |
| 5,385,140 A | 1/1995 | Smith |
| 5,408,994 A | 4/1995 | Wass et al. |
| 5,409,144 A | 4/1995 | Brown |
| 5,419,315 A | 5/1995 | Rubsamen |
| 5,435,301 A | 7/1995 | Herold et al. |
| 5,437,271 A | 8/1995 | Hodson et al. |
| 5,439,143 A | 8/1995 | Brown et al. |
| 5,447,150 A | 9/1995 | Bacon |
| 5,447,151 A | 9/1995 | Bruna et al. |
| 5,458,135 A | 10/1995 | Patton et al. |
| 5,483,954 A | 1/1996 | Mecikalski |
| 5,509,404 A | 4/1996 | Lloyd et al. |
| 5,513,630 A | 5/1996 | Century |
| 5,522,380 A | 6/1996 | Dwork |
| 5,529,059 A | 6/1996 | Armstrong et al. |
| 5,533,505 A | 7/1996 | Kallstrand et al. |
| 5,542,412 A | 8/1996 | Century |
| 5,558,085 A | 9/1996 | Rubsamen et al. |
| 5,568,807 A | 10/1996 | Mecikalski |
| 5,586,550 A | 12/1996 | Ivri et al. |
| 5,617,845 A | 4/1997 | Poss et al. |
| 5,622,166 A | 4/1997 | Eisele et al. |
| 5,653,223 A | 8/1997 | Pruitt |
| 5,654,007 A | 8/1997 | Johnson et al. |
| 5,655,520 A | 8/1997 | Howe et al. |
| 5,672,581 A | 9/1997 | Rubsamen et al. |
| 5,692,492 A | 12/1997 | Bruna et al. |
| 5,692,496 A | 12/1997 | Casper et al. |
| 5,692,498 A | 12/1997 | Lurie et al. |
| 5,699,789 A | 12/1997 | Hendricks |
| 5,724,959 A | 3/1998 | McAughey et al. |
| 5,727,546 A | 3/1998 | Clarke et al. |
| 5,740,794 A | 4/1998 | Smith et al. |
| 5,775,320 A | 7/1998 | Patton et al. |
| 5,785,049 A | 7/1998 | Smith et al. |
| 5,813,401 A | 9/1998 | Radcliff et al. |
| 5,823,183 A | 10/1998 | Casper et al. |
| 5,826,571 A | 10/1998 | Casper et al. |
| 5,826,633 A | 10/1998 | Parks et al. |
| 5,855,202 A | 1/1999 | Andrade |
| 5,873,358 A | 2/1999 | Gonda et al. |
| 5,875,776 A | 3/1999 | Vaghefi |
| 5,881,719 A | 3/1999 | Gottenauer et al. |
| 5,884,620 A | 3/1999 | Gonda et al. |
| 5,896,853 A | 4/1999 | Howlett |
| 5,921,237 A | 7/1999 | Eisele et al. |
| 5,922,354 A | 7/1999 | Johnson et al. |
| 5,941,240 A | 8/1999 | Gonda et al. |
| 5,975,076 A | 11/1999 | Yianneskis et al. |
| 5,983,893 A | 11/1999 | Wetterlin |
| 5,988,163 A | 11/1999 | Casper et al. |
| 5,993,421 A | 11/1999 | Kriesel |
| 6,006,747 A | 12/1999 | Eisele et al. |
| 6,012,454 A | 1/2000 | Hodson et al. |
| 6,029,661 A | 2/2000 | Whaley et al. |
| 6,029,663 A | 2/2000 | Eisele et al. |
| 6,055,979 A | 5/2000 | Fuchs |
| 6,055,980 A * | 5/2000 | Mecikalski et al. ..... 128/203.15 |
| 6,062,219 A | 5/2000 | Lurie et al. |
| 6,065,472 A | 5/2000 | Anderson et al. |
| 6,070,573 A | 6/2000 | Howe et al. |
| 6,076,523 A | 6/2000 | Jones et al. |
| 6,085,753 A | 7/2000 | Gonda et al. |
| 6,089,228 A | 7/2000 | Smith et al. |
| 6,095,134 A | 8/2000 | Sievers et al. |
| 6,102,036 A | 8/2000 | Slutsky et al. |
| 6,105,574 A | 8/2000 | Jahnsson |
| 6,109,261 A | 8/2000 | Clarke et al. |
| 6,116,237 A | 9/2000 | Schutlz et al. |
| 6,116,238 A | 9/2000 | Jackson et al. |
| 6,116,239 A | 9/2000 | Volgyesi |
| 6,138,673 A | 10/2000 | Sherherd |
| 6,142,146 A | 11/2000 | Abrams et al. |
| 6,606,992 B1 * | 8/2003 | Schuler et al. ......... 128/203.15 |

FOREIGN PATENT DOCUMENTS

| | | |
|---|---|---|
| HU | 214757 | 10/1993 |
| HU | 212398 | 5/1994 |
| HU | 219215 | 11/1996 |
| WO | 91/14422 | 10/1991 |
| WO | 95/24183 | 9/1995 |
| WO | 95/34337 | 12/1995 |
| WO | 96/09085 | 3/1996 |
| WO | 96/30068 | 10/1996 |
| WO | 96/32149 | 10/1996 |
| WO | 97/40819 | 11/1997 |
| WO | 98/32479 | 7/1998 |
| WO | 99/16419 | 4/1999 |
| WO | 99/27987 | 6/1999 |
| WO | 99/46055 | 9/1999 |
| WO | 99/47196 | 9/1999 |
| WO | 00/01435 | 1/2000 |
| WO | 00/21594 | 4/2000 |
| WO | 01/00263 | 1/2001 |

OTHER PUBLICATIONS

Chrystyn, "The Diskus® Inhaler—A Review of its Pharmaceutical and Clinical Performance," *Clinical Drug Investigations*™, *[Clin Drug Invest* 18(4):287-296, 1999. © 1999 Adis International Limited].

Clark et al., "The Relationship Between Powder Inhaler Resistance and Peak Inspiratory Conditions in Healthy Volunteers—Implications for In Vitro Testing," J. of Aerosol Med., vol. 6, No. 2, 1993, pp. 99-110.

Clark, "Effect of Powder Inhaler Resistance Upon Inspiratory Profiles in Health and Disease," Respiratory Drug Delivery IV, 1994, pp. 117-123.

Conway et al., "Comparison of Peak Pressure Drops Through Powder Inhalers During Inspiration at Maximum Flow Rate," [Abstract] American J. of Respiratory and Critical Care Med., vol. 153, No. 4, A59, Apr. 1996.

Dolovich, "Physical Principles Underlying Aerosol Therapy," J. of Aerosol Med., vol. 2, No. 2, 1989, pp. 171-186.

Elliot et al., "Parenteral absorption of insulin from the lung in diabetic children," Aust. Paediatr. J. (1987) 23, 293-297.

Hill, "Characteristics of an Active, Multiple Dose Dry Powder Inhaler," Respiratory Drug Delivery IV, 1994, pp. 109-116.

Lawford et al., "Pressurized Aerosol Inhaler Technique: How Important are Inhalation from Residual Volume, Inspiratory Flow Rate and the Time Interval Between Puffs?" Br. J. Dis. Chest (1983) 77, 276-281.

Malton et al., "A comparison of in vitro drug delivery from two multidose powder inhalation devices," European J. of Clinical Research 1995, 7:177-193.

Malton et al., A comparison of in-vitro drug delivery from salbutamol Diskus and terbutaline Turbohaler inhalers, J. Pharm. Med. (1996) 6, 35-48.

Nantel et al., "Flow Targeting System for DPI Clinical Trials," J. of Aerosol Med., vol. 8, No. 1, 1995, P136, p. 103.

Newhouse et al., "Clickhaler (a Novel Dry Powder Inhaler) Provides Similar Bronchodilation to Pressurized Metered-Dose Inhaler, Even at Low Flow Rates," Chest, vol. 115, No. 4, pp. 952-956, Apr. 1999.

Prime et al., "The Flixotide™ Diskus™, a new multi dose powder inhaler—in-vitro evaluation using an inhalation simulator," J. of Aerosol Med., vol. 8, No. 1, 1995, P137, p. 103.

Prime et al., "The Flixotide™ Diskus™, a new multi dose powder inhaler—consistency of dose and fine particle mass, protection from moisture," J. of Aerosol Med., vol. 8, No. 1, 1995, P138, p. 103.

Robertson et al., "The influence of (pseudo) polymorphic forms of lactose on dry powder inhaler performance," J. of Aerosol Med., vol. 8, No. 1, 1995, P139, p. 103.

Ross et al., "Effect of Inhalation Flow Rate on the Dosing Characteristics of Dry Powder Inhaler (DPI) and Metered Dose Inhaler (MDI) Products," J. of Aerosol Med., vol. 9, No. 2, 1996, pp. 215-226.

* cited by examiner

FLOW REGULATOR FOR AEROSOL DRUG DELIVERY AND METHODS

BACKGROUND OF THE INVENTION

This invention relates generally to the field of drug delivery, and in particular to the delivery of pharmaceutical formulations to the lungs. More specifically, the invention relates to the aerosolization of pharmaceutical formulations using air flows created by patient inhalation, and to the regulation of such air flows such that the pharmaceutical formulation is provided to the patient within a desired flow rate range.

Effective drug delivery to a patient is a critical aspect of any successful drug therapy, and a variety of drug delivery techniques have been proposed. For example, one convenient method is the oral delivery of pills, capsules, elixirs and the like. However, oral delivery can in some cases be undesirable in that many drugs are degraded in the digestive tract before they can be absorbed. Another technique is subcutaneous injection. One disadvantage to this approach is low patient acceptance. Other alternative routes of administration that have been proposed include transdermal, intranasal, intrarectal, intravaginal and pulmonary delivery.

Of particular interest to the invention are pulmonary delivery techniques which rely on the inhalation of a pharmaceutical formulation by the patient so that the active drug within the dispersion can reach the distal (alveolar) regions of the lung. A variety of aerosolization systems have been proposed to disperse pharmaceutical formulations. For example, U.S. Pat. Nos. 5,785,049 and 5,740,794, the disclosures of which are herein incorporated by reference, describe exemplary powder dispersion devices which utilize a compressed gas to aerosolize a powder. Other types of aerosolization systems include MDI's (which typically have a drug that is stored in a propellant), nebulizers (which aerosolize liquids using compressed gas, usually air), and the like.

Another technique which is of interest to the invention is the use of inspired gases to disperse the pharmaceutical formulation. In this way, the patient is able to provide the energy needed to aerosolize the formulation by the patient's own inhalation. This insures that aerosol generation and inhalation are properly synchronized. Utilization of the patient's inspired gases can be challenging in several respects. For example, for some pharmaceutical formulations, such as insulin, it may be desirable to limit the inhalation flow rate within certain limits. For example, PCT/US99/04654, filed Mar. 11, 1999, provides for the pulmonary delivery of insulin at rates less than 17 liters per minute. As another example, copending U.S. patent application Ser. No. 09/414,384 describes pulmonary delivery techniques where a high flow resistance is provided for an initial period followed by a period of lower flow resistance. The complete disclosures of all the above references are herein incorporated by reference.

Another challenge in utilizing the patient's inspired gases is that the inspiration flow rate can drastically vary between individuals. For instance, individuals can inhale to produce flow rates ranging from about 5 liters per minute to about 35 liters per minute, or even greater. Such variability may affect the ability of the formulation to be dispersed within a gas stream, the ability to deagglomerate a powdered formulation, and/or the ability of the aerosolized formulation to adequately reach the deep lung. Copending U.S. patent application Ser. Nos. 09/312,434, filed May 14, 1999 and Ser. No. 09/583,312, filed May 30, 2000 and PCT Publication Nos. WO 99/62495 and WO 01/00263 describe various techniques for regulating inspiration flow rates. The complete disclosures of these references are herein incorporated by reference.

This invention is related to other techniques for regulating the flow of inspired gases that may be utilized when dispersing a pharmaceutical formulation. In one aspect, the invention is related to various valves that may be used to regulate the flow of such gases.

SUMMARY OF THE INVENTION

The invention provides techniques for regulating gas flows, especially those used to aerosolize powders, as well as inhalation devices and components of such devices that facilitate gas flow regulation. In one embodiment, gas flows are regulated using a flow path arrangement having a flow regulating valve and a threshold valve. The threshold valve is configured to open at a first vacuum level and to close at a second vacuum level that is less than the first vacuum level. A vacuum is produced within the flow path arrangement that is sufficient to open the threshold valve and to permit a gas to exit the flow path arrangement at a certain flow rate. This vacuum may conveniently be produced by patient inhalation. Once the threshold valve is open, the flow rate is maintained within a specified range until the threshold valve resets at a lower vacuum than that required to open the threshold valve. By placing an amount of powder in fluid communication with the flow path arrangement, the abrupt opening of the threshold valve creates a gas flow sufficient to aerosolize the powder. Further, the flow regulating valve regulates the flow rate to be within a certain range while the threshold valve remains open. By utilizing the threshold valve with the lower reset second vacuum level, the patient may reduce the vacuum below the opening vacuum of the threshold valve but still produce enough of a vacuum to keep the valve open and to maintain the flow rate within the desired range. If an excessive vacuum is produced, the flow regulating valve is used to increase flow resistance and thereby maintain a constant or near constant flow rate through the flow path arrangement.

In one aspect, the flow path arrangement has a series-parallel configuration with a first flow path that divides into a second flow path and a third flow path. Further, the threshold valve is in the first flow path, the flow regulating valve is in the second flow path, and the powder is coupled to the third flow path. With such a configuration, the flow regulating valve closes at a greater rate to provide an increased flow resistance as the vacuum increases, i.e., the flow regulating valve has a highly non-linear orifice area/vacuum relationship, to maintain the total flow rage within the desired range.

In another aspect, the first vacuum level is in the range from about 20 cm $H_2O$ to about 50 cm $H_2O$, more preferably from about 25 cm $H_2O$ to about 40 cm $H_2O$, and more preferably about 35 cm $H_2O$, and the second vacuum level is in the range from about 0 cm $H_2O$ to about 12 cm $H_2O$, and more preferably from about 0 cm $H_2O$ to about 8 cm $H_2O$. The flow rate may be regulated to be within the range of about 10 liters/min to about 20 liters/min, and more preferably from about 12 liters/min to about 16 liters/min for a wide range of vacuum levels between about 15 cm $H_2O$ to about 80 cm $H_2O$.

In one particular configuration, the flow regulating valve comprises at least one deformable wall and an opposing surface. The deformable wall moves toward the opposing surface as the vacuum downstream of the flow regulating valve increases, thereby increasing flow resistance to regulate the flow rate. For example, in one embodiment, the flow regulating valve comprises a valve body having an inlet end, an outlet end and a gas flow passage between the inlet end and the outlet end. The valve body is constructed of a resilient material and the valve body at the outlet end has a central region and a plurality of extending regions that extend outwardly from the central region. The extending regions are drawn together to limit the flow of gases through the gas flow passage as the vacuum at the outlet end increases. Further, such an embodiment has a highly non-linear orifice area/vacuum relationship so that the valve closes rapidly as higher vacuums are produced. Further, the valve body may include a boundary layer step just beyond the inlet to insure boundary layer separation. In this way, the valve operates in a predictable manner across a wide range of vacuums and flow rates.

The powder may conveniently be contained within a receptacle so that the gas flow through the flow path arrangement flows through the receptacle to extract and aerosolize the powder. In a further aspect, the flow path arrangement is coupled to a mouthpiece to permit the vacuum to be produced by inhaling through the mouthpiece.

In another embodiment, the invention provides an exemplary aerosolization device that comprises a housing having a mouthpiece and a flow path arrangement that is in fluid communication with the mouthpiece. The flow path arrangement has a flow regulating valve and a threshold valve, and the threshold valve is configured to open at a first vacuum level and to close at a second vacuum level that is less than the first vacuum level. The housing includes a region that is adapted to hold a powder in fluid communication with the flow path arrangement so that when air is drawn through the mouthpiece, the threshold valve opens once the first vacuum level is exceeded. The threshold valve remains open until the vacuum level falls below the second vacuum level. Further, the flow rate of the air drawn through the mouthpiece is regulated by the flow regulating valve to remain within a certain range while the threshold valve remains open.

In one aspect, the flow path arrangement has a first flow path that divides into a second flow path and a third flow path. Further, the threshold valve is in the first flow path, the flow regulating valve is in the second flow path, and the powder is coupled to the third flow path. The second flow path and the third flow path may then combine at a region just prior to the mouthpiece.

The device may be configured so that the first vacuum level is in the range from about 20 cm $H_2O$ to about 50 cm $H_2O$, more preferably from about 25 cm $H_2O$ to about 40 cm $H_2O$, and more preferably about 35 cm $H_2O$, and the second vacuum level is in the range from about 0 cm $H_2O$ to about 12 cm $H_2O$, and more preferably from about 0 cm $H_2O$ to about 8 cm $H_2O$. The flow regulating valve may also be configured to regulate the flow rate below about 20 liters/min and more preferably below about 16 liters/min over a wide range of vacuums, such as between about 15 cm $H_2O$ and about 80 cm $H_2O$.

In one aspect, the device is used with a receptacle that is configured to be held within the housing. The receptacle has a chamber that is adapted to hold the powder. In this way, the receptacle may be coupled to the third flow path to permit the gas to flow through the receptacle chamber to extract and aerosolize the powder.

In a further aspect, the flow regulating valve comprises at least one deformable wall and an opposing surface. The deformable wall moves toward the opposing surface as the vacuum downstream of the flow regulating valve increases to regulate the flow rate.

The invention further provides an exemplary valve that may conveniently be used as a flow regulating valve in an aerosolization device. The valve comprises a valve body having an inlet end, an outlet end and a gas flow passage between the inlet end and the outlet end. The valve body is constructed of a resilient material, and the valve body at the outlet end has a central region and a plurality of extending regions that extend outwardly from the central region. In this way, the extending regions are drawn together to limit the flow of gases through the gas flow passage as the vacuum downstream increases. Hence, when used in an aerosolization device, the valve may be used to limit the flow rate to be within certain limits. At low vacuums, the valve remains fully open so that adequate flow rates may be achieved.

In one aspect, each extending region comprises a pair of walls having a base end and a top end, and the top ends are connected at an acute angle. Further, each extending region is connected to two adjacent extending regions at the base ends of the walls to define the central region. In one arrangement, the number of extending regions is eight. With such a configuration, the outlet end may include two orthogonal axis, with one of the axis passing through two of the extending regions, and the other orthogonal axis passing through the other two extending regions. A variety of elastomeric materials may be used to construct the valve, such as silicone rubber. Such materials maintain generally constant mechanical properties over a wide range of temperatures, such as between about −40° C. to about 200° C.

DEFINITIONS

"Active agent" as described herein includes an agent, drug, compound, composition of matter or mixture thereof which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized or systemic effect in a patient. The active agent that can be delivered includes antibiotics, antiviral agents, anepileptics, analgesics, anti-inflammatory agents and bronchodilators, and viruses and may be inorganic and organic compounds, including, without limitation, drugs which act on the peripheral nerves, adrenergic receptors, cholinergic receptors, the skeletal muscles, the cardiovascular system, smooth muscles, the blood circulatory system, synaptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, polysaccharides, steroids, hypnotics and sedatives, psychic energizers, tranquilizers, anticonvulsants, muscle relaxants, antiparkinson agents, analgesics, anti-inflammatories, muscle contractants, anti-infectives, antibiotics, antimicrobials, antimalarials, hormonal agents including contraceptives, sympathomimetics, polypeptides, and proteins capable of eliciting physiological effects, diuretics, lipid regulating agents, antiandrogenic agents, antiparasitics, neoplastics, antineoplastics, hypoglycemics, nutritional agents and supplements, growth supplements, fats, antienteritis agents, electrolytes, vaccines and diagnostic agents.

Examples of active agents useful in this invention include but are not limited to insulin, calcitonin, erythropoietin (EPO), Factor VIII, Factor IX, ceredase, cerezyme, cyclosporine, granulocyte colony stimulating factor (GCSF), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-2, luteinizing hormone releasing hormone (LHRH), somatostatin, somatostatin analogs including octreotide, vasopressin analog, follicle stimulating hormone (FSH), insulin-like growth factor, insulintropin, interleukin-1 receptor antagonist, interleukin-3, interleukin-4, interleukin-6, macrophage colony stimulating factor (M-CSF), nerve growth factor, parathyroid hormone (PTH), thymosin alpha 1, IIb/IIIa inhibitor, alpha-1 antitrypsin, respiratory syncytial virus antibody, cystic fibrosis transmembrane regulator (CFTR) gene, deoxyribonuclease (Dnase), bactericidal/permeability increasing protein (BPI), anti-CMV antibody, interleukin-1 receptor, 13-cis retinoic acid, pentamidine isethionate, albuterol sulfate, metaproterenol sulfate, beclomethasone dipropionate, triamcinolone acetamide, budesonide acetonide, ipratropium bromide, flunisolide, fluticasone, cromolyn sodium, nicotine, lung surfactant, amphotericin B, ciprofloxacin, gentamicin, tobramycin, ergotamine tartrate and the analogues, agonists and antagonists of the above. Active agents may further comprise nucleic acids, present as bare nucleic acid molecules, viral vectors, associated viral particles, nucleic acids associated or incorporated within lipids or a lipid-containing material, plasmid DNA or RNA or other nucleic acid construction of a type suitable for transfection or transformation of cells, particularly cells of the alveolar regions of the lungs. The active agents may be in various forms, such as soluble and insoluble charged or uncharged molecules, components of molecular complexes or pharmacologically acceptable salts. The active agents may be naturally occurring molecules or they may be recombinantly produced, or they may be analogs of the naturally occurring or recombinantly produced active agents with one or more amino acids added or deleted. Further, the active agent may comprise live attenuated or killed viruses suitable for use as vaccines.

DESCRIPTION OF THE SPECIFIC EMBODIMENTS

The invention provides systems and methods for the administration of aerosolized pharmaceutical formulations using the flow of respiratory gases produced by a patient. The pharmaceutical formulations that may be aerosolized include powdered medicaments, liquid solutions or suspensions, and the like, and may include an active agent. The devices of the present invention may be used for single or multiple administrations.

In some embodiments, the flow of respiratory gases produced by the patient is employed to extract the pharmaceutical formulation from a receptacle, to deagglomerate the pharmaceutical formulation and deliver the pharmaceutical formulation to the patient's lungs. One particular advantage of the invention is the ability to perform such functions independent of the patient's natural inhalation flow rate. Hence, in one aspect of the invention, the inhaled respiratory gases are controlled so that they remain within an acceptable range of flow rates to adequately deliver the pharmaceutical formulation to the lungs. In this way, aerosolized drugs may be efficiently, accurately and repeatably be delivered to the patient. As described hereinafter, the invention provides techniques for limiting the flow rate if the patient produces an excessive vacuum during inhalation, as well as techniques for reducing flow resistances so that patients producing a low vacuum during inhalation still achieve an acceptable flow rate. In one aspect, the invention is configured to maintain the flow rate within a range of about 10 liters/min to about 20 liters/min, and more preferably from about 12 liters/min to about 16 liters/min during the inhalation maneuver.

In another aspect, the invention is configured to regulate the flow of inspired gases so that the gases have sufficient energy to extract the pharmaceutical formulation from a receptacle, deagglomerate the formulation, and deliver it to the patient's lungs. As mentioned above, the invention is further configured to maintain the inhalation flow rate below a maximum level for at least a certain time or inhaled volume when initially delivering the drug. In this way, the aerosolized formulation will flow at an acceptable flow rate to enhance its ability to traverse the patient's airway and enter into the lungs.

Further, the invention also provides techniques to help insure that flow rates are maintained above a minimal level during inhalation. Such techniques may be needed, for example, when the patient is unable to maintain a sufficient vacuum during inhalation due to reduced lung capacity or when near the end of inspiratory effort. The techniques reduce the flow resistance at low vacuums so that patients that are unable to maintain higher vacuums may still produce acceptable flow rates.

To aerosolize the pharmaceutical formulation, the flow of respiratory gases preferably contains sufficient energy to extract the pharmaceutical formulation from the receptacle. To ensure that the respiratory gases contain sufficient energy, the invention may be configured to prevent respiratory gases from flowing to the patient's lungs when the patient attempts to inhale. Abruptly, the respiratory gases may then be permitted to flow to the patient's lungs after a threshold vacuum has been reached. By abruptly permitting the flow of respiratory gases only when sufficient vacuum has been applied by the user, a relatively high rate of flow is achieved to provide the gas stream with sufficient energy. One way to accomplish such a process is by placing a restriction, valve, or other blocking mechanism in the patient's airway to prevent respiratory gases from entering the patient's lungs when the patient attempts to inhale. The restriction or valve may then be rapidly removed or opened to permit respiratory gases to flow to the lungs. Hence, a patient may be instructed to inhale until a threshold actuating vacuum is overcome. The threshold actuating vacuum may be configured such that it will produce sufficient energy in the resulting gas stream when the gases are allowed to flow to the patient's lungs. Preferably, the threshold vacuum is in the range from about 20 cm $H_2O$ to about 50 cm $H_2O$ so that the resulting gas stream will have sufficient energy to extract and deagglomerate the pharmaceutical formulation. More preferably, the threshold vacuum is about 25 cm $H_2O$ to about 40 cm $H_2O$.

A variety of threshold valves may also be employed to prevent respiratory gases from reaching the patient's lungs until a threshold inhalation vacuum is obtained. For example, the threshold valve may comprise an elastically compliant valve such as a flexible membrane that is disposed across the airway and is configured to flex when the threshold vacuum is met or exceeded. Alternatively, the threshold valve may comprise a scored membrane that is configured to tear or burst once the threshold vacuum is met or exceeded. As another example, the threshold valve may comprise an elastomer membrane having an opening. A ball is pulled through the opening once the threshold vacuum has been met or exceeded. Other types of threshold valves include bi-stable mechanisms, diaphragms, and the like.

One particular embodiment of a threshold valve closes at a lower vacuum than is used to open the valve. With such a configuration, the threshold valve will remain open even if the patient is unable to maintain the same vacuum required to open the valve. As such, acceptable flow rates may still be achieved, even if the vacuum produced by the patient falls below the opening vacuum level of the valve. In this way, sufficient energy is obtained to extract and aerosolize the medicament while providing the patient with the ability to maintain an acceptable flow rate as the patient's ability to maintain a high vacuum diminishes. For example, the opening threshold vacuum may be in the range from about 20 cm $H_2O$ to about 45 cm $H_2O$, and more preferably from about 25 cm $H_2O$ to about 40 cm $H_2O$, while the closing vacuum is in the range from about 0 cm $H_2O$ to about 12 cm $H_2O$, and more preferably from about 0 cm $H_2O$ to about 8 cm $H_2O$.

The threshold valve may be an automatically resetting valve or require mechanically resetting after opening. In the latter case, the valve remains in an open state until actively closed by the user. As such, regardless of the vacuum produced by the user, the valve remains open. A resetting mechanism may be used to reset the valve after an inhalation maneuver. Examples of such valves include those having a membrane through which a ball passes as well as those described in copending U.S. application Ser. No. 09/583,312 previously incorporated by reference.

The automatically resetting valves of the invention may be configured to reset at some small user applied vacuum, such as below about 12 cm $H_2O$, and preferably less than 8 cm $H_2O$. In this way, the user is not required to reset the valve after inhaling a medication. Moreover, such a valve may be of relatively simple construction. For example, the threshold valve may be constructed of a bistable silicone rubber component that moves between a closed position and an open position as dictated by an upper threshold vacuum and a lower threshold vacuum. Examples of such valves are described in U.S. Pat. Nos. 4,991,754; 5,033,655; 5,213, 236; 5,339,995; 5,377,877; 5,439,143; and 5,409144, the complete disclosures of which are herein incorporated by reference. The rubber component may be cup shaped and is inverted as it moves to the open position. One or more slits are provided that open up as the rubber component inverts. With such a configuration, the valve is virtually sealed and remains in the closed position until an upper threshold vacuum is achieved to invert the valve. The valve also resists back flow while in the closed position. Once inverted to the open position, free flow through the valve is permitted with little resistance. Further, the valve remains open with a minimal user produced vacuum.

To maintain the flow rate within a certain range, a flow regulating valve may be used that is completely open at low vacuums and begins to close at higher vacuums. In this way, users producing a low vacuum experience little or no resistance during continued inhalation while users producing a high vacuum experience some resistance as the valve closes to limit the flow rate. In this way, users producing low vacuums are not prematurely cut-off. Also, these users do not feel "starved" for air during inhalation maneuver. In one embodiment, such a flow regulating valve may comprise a resilient material with one or more deformable walls that move to close a flow path as the vacuum is increased.

To help insure that the threshold valve remains open at low vacuum levels, the threshold valve and the flow regulating valve act in concert. The flow regulating valve opens to lower flow resistance and increases the system flow rate more than is necessary to keep the flow rate constant as the vacuum falls. In this way, the system flow rate slightly increases. For example, the system flow rate may increase about 1 liter/min as the system vacuum falls from about 25 cm $H_2O$ to about 18 cm $H_2O$. This exaggerated drop in resistance across the flow regulating valve at low vacuum results in a larger proportion of the total system vacuum falling across the threshold valve, helping to keep it open down to levels below 12 cm $H_2O$, and more preferably below 5 cm $H_2O$. The increase in flow rate at low vacuum provides the user with the perception of reduced inspiratory effort.

Devices according to the invention may utilize either series or series-parallel flow paths. For example, the threshold valve and the flow regulating valve may be along the same flow path where the powder is introduced. Preferably, the flow regulating valve may be in a flow path that is parallel to the flow path where the powder is introduced. For series arrangements, the flow resistance/vacuum relationship is close to approaching a linear relationship. For parallel arrangements, the flow resistance/vacuum relationship is preferably highly non-liner. In either case, the threshold valve may be configured to have a closing vacuum level that is lower than the opening vacuum level so that patients that produce low vacuums may still achieve acceptable flow rates.

Devices according to the invention may have an entire flow path system with the threshold valve and the flow regulating valve as an integrated unit. Alternatively, parts of the flow path arrangement and/or the valves may be included as an add on unit so that an existing aerosolization device may be modified to regulate the flow rate.

Figure 1:
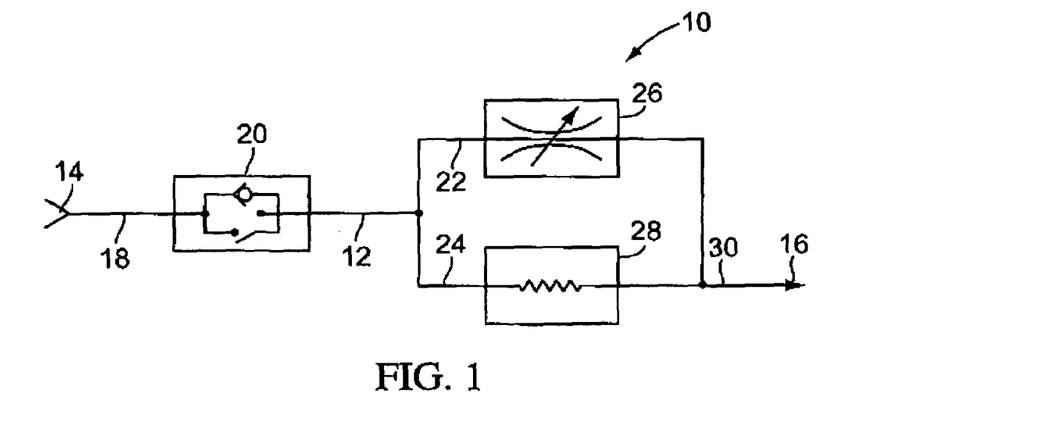
FIG. 1 is a schematic diagram of an aerosolization device according to the invention.

Referring now to FIG. 1, one embodiment of an aerosolization device 10 will be described schematically. Device 10 will typically be contained within a housing (not shown) which includes a flow path arrangement 12. Flow path arrangement 12 is a series-parallel arrangement and has an inlet end 14 that may terminate at an opening in the housing and an outlet end 16 that terminates at a mouthpiece. A first flow path 18 extends from inlet end 14 and includes a threshold valve 20. Threshold valve 20 is configured to be in a closed position where gases are prevented from flowing from inlet end 14 to outlet end 16 until an opening threshold vacuum level is exceeded. Such a vacuum may be produced by patient inhalation at outlet end 16. When this opening vacuum level is exceeded, valve 20 opens to permit gases to flow through first flow path 18 and into a second flow path 22 and a third flow path 24 which are in parallel. Valve 20 is further configured to close at a threshold closing vacuum level that is lower in absolute value than the opening vacuum level. In this way, if the patient is unable to maintain a vacuum higher than the opening vacuum level, valve 20 will remain open.

The opening vacuum level of valve 20 is set such that sufficient energy is produced to extract and aerosolize a powder as described hereinafter. Such an opening vacuum level may be in the range from about 20 cm $H_2O$ to about 50 cm $H_2O$, and more preferably from about 25 cm $H_2O$ to about 40 cm $H_2O$. The closing vacuum level of valve 20 is set so that users who are unable to maintain high vacuums are still able to keep valve 20 open while achieving an adequate flow rate. If this flow rate is unable to be achieved, valve 20 closes. Such closing vacuum levels may be in the range from about 0 cm $H_2O$ to about 12 cm $H_2O$, and preferably from about 0 cm $H_2O$ to about 8 cm $H_2O$.

Figure 2A:
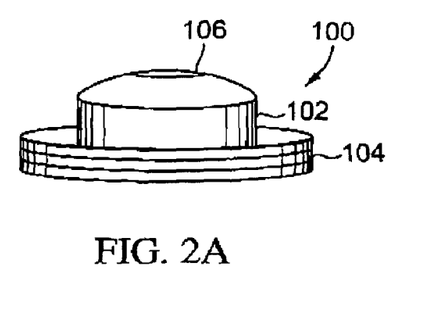
FIG. 2A is a perspective view of one embodiment of a threshold valve according to the invention shown in a closed position.
Figure 2B:
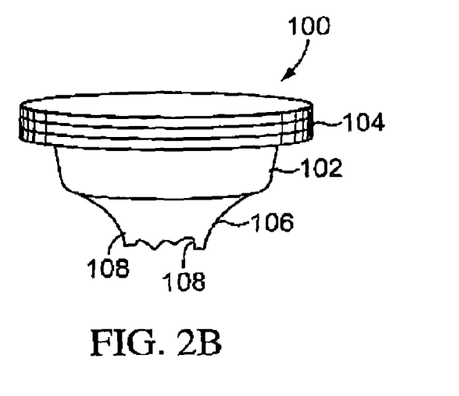
FIG. 2B illustrates the threshold valve of FIG. 2A in an open position.

One type of valve that may be configured to close at a vacuum level that is lower than the opening vacuum level is illustrated in FIGS. 2A and 2B. Shown in FIGS. 2A and 2B is a bistable threshold valve 100 that compresses an invertable valve body 102 that may be constructed of an elastomer, such as silicone rubber. Valve body 102 has a base 104 that may be used to couple valve 100 within a conduit and a head 106. Head 106 includes a pair of slits 108 that form an "X" shape in head 106. In FIG. 2A, valve 100 is shown in the closed position where slits 108 are closed to permit gas flow through valve 100. When a threshold vacuum is achieved, valve 100 inverts to the position shown in FIG. 2B. In so doing, slits 108 open to prevent gas flow through valve 100. Valve 100 may be maintained in the open configuration at a vacuum that is lower than that required for opening. At low vacuums, valve 100 automatically rests back to the closed position.

The opening and closing vacuum levels may be varied by changing the thickness of head 106, the length of slits 108 and the shape of slits 108. For example, making head 106 thicker causes a higher threshold opening vacuum, a higher flow resistance, a higher closing vacuum and a more robust closure. Making slits 108 longer provides a lower flow resistance, a lower closing vacuum and a less robust closure.

Disposed in flow path 22 is a flow regulating valve 26, and coupled to flow path 24 is a receptacle 28 containing a powder to be aerosolized. Flow paths 22 and 24 join together into a fourth flow path 30 that leads to outlet end 16. The flow rate through each flow path 22 and 24 is controlled by the resistance of receptacle 28 and the configuration of flow regulating valve 26. The resistance of receptacle 28 is generally constant and is based on the configuration of the receptacle, while the resistance of valve 26 is highly variable. More specifically, valve 26 is configured to remain fully open (and thus provide little or no resistance) at low vacuums and to progressively provide greater resistances at higher vacuums. In this way, as the vacuum applied by the user increases, valve 26 closes to the extent needed such that the flow rate through outlet end 16 remains within a generally constant range. If the flow rate falls below a lowest possible user applied vacuum that is consistent with secure closure within a short time (typically less than about 2 seconds) after the end of the user's inspiratory effort, valve 20 closes. This is typically less than about 12 cm $H_2O$, and more preferably less than 8 cm $H_2O$. Valve 26 in one embodiment is preferably configured to maintain the flow rate through outlet end 16 in the range from about 12 liters/min to about 16 liters/min for vacuums levels between about 15 cm $H_2O$ and about 80 cm $H_2O$.

A variety of receptacles may be used to hold the powder. For example, the receptacle may include a chamber or cavity that holds a powder and has a penetrable access lid that may be pierced to gain access to the powder. Examples of receptacles that may be used, as well as techniques for accessing the powder are described in U.S. Pat. Nos. 5,785,049; 5,740,794 and 6,089,228, and in copending U.S. application Ser. Nos. 09/312,434, filed May 14, 1999 and Ser. No. 09/556,262, filed Apr. 24, 2000, the complete disclosures of which are herein incorporated by reference.

When used in a series-parallel flow path arrangement, the flow regulating valve 26 may have a highly non-linear relationship between the cross sectional area and the applied vacuum. In this way, the valve may close to a greater extent as the vacuum level is increased to counteract the flow through the parallel flow path. In some embodiments, vales 20 and 26 may be in series with receptacle 20. For example, flow regulating valve 26 may be followed by receptacle 28. Each component therefore experiences essentially the same flow rate at any given time. As such, flow regulating valve 26 behaves differently as described hereinafter.

Figure 3:
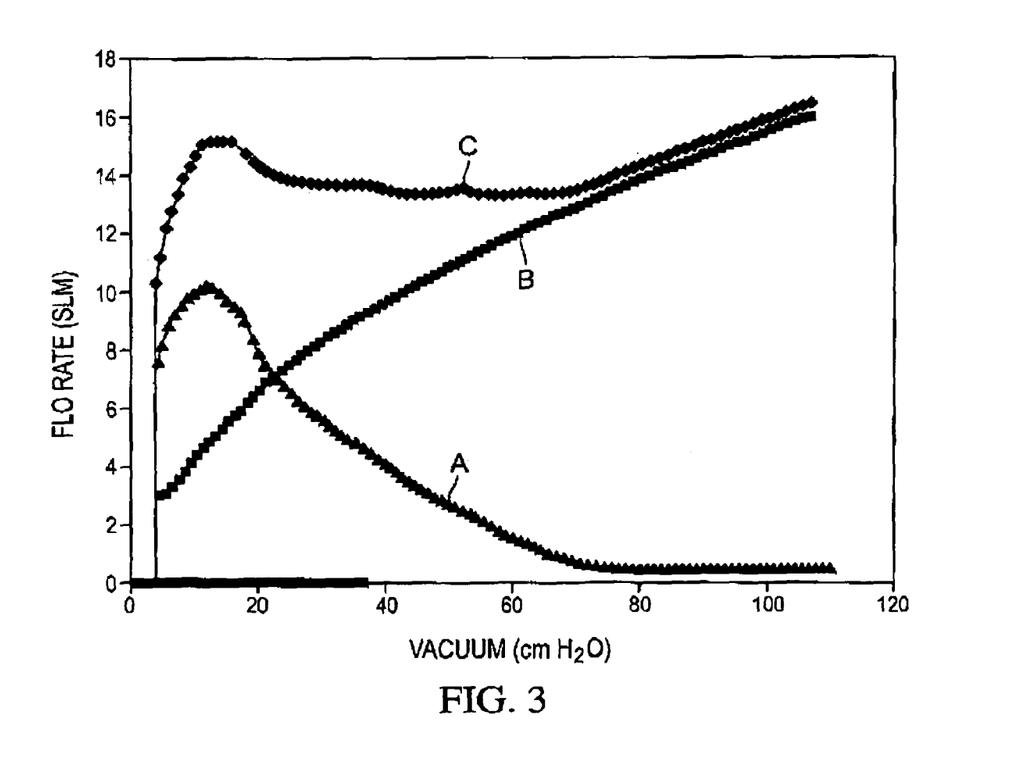
FIG. 3 is a graph illustrating the relationship between an applied vacuum and the flow rate through the aerosolization device of FIG. 1.

FIG. 3 illustrates the relationship between the vacuum applied by a user to the flow rate through various portions of the flow path arrangement 12 for one configuration of aerosolization device 10. The graph of FIG. 3 has three lines A, B, and C that represent the flow rate and vacuum at flow regulating valve 26, at receptacle 28 and at outlet end 16, respectively. In the graph of FIG. 3, threshold valve 20 is assumed to already have been opened, and closes when the vacuum falls below about 5 cm $H_2O$. While valve 20 is opened, as the vacuum is increased, valve 26 progressively closes to decrease the flow rate through flow path 22. The flow rate through receptacle 28 increases with the increased vacuum. As such valve 26 is configured to decrease the flow rate by an amount such that the total flow at outlet end 16 remains generally constant, i.e., within a range of about 12 liters/min to about 16 liters/min. At a vacuum of about 80 cm $H_2O$, valve 26 is completely closed; however, since most people are incapable of sustaining such a high level of vacuum, the total flow remains generally constant within reasonable vacuum ranges.

Hence, with aerosolization device 10, a patient is required to produce a vacuum sufficient to open threshold valve 20. This creates enough energy to ensure that the powder in receptacle 28 is extracted and aerosolized. Once the initial release of energy has occurred, device 10 is configured to maintain the flow rate at the mouthpiece to be within a narrow range to ensure efficient, accurate and repeatable dosings. A minimal flow rate is guaranteed based on the closing vacuum level of valve 20. As long as enough vacuum is produced to keep valve 20 open, a flow rate of at least 12 liters/min is achieved. If the applied vacuum is too great, valve 26 closes to decrease the overall flow rate.

As shown in FIG. 3, the flow rate of line C increases or jumps when the vacuum drops below about 25 cm $H_2O$ until reaching about 18 cm $H_2O$. This increase is produced as flow regulating valve 26 opens to lower flow resistance as the vacuum falls. This drop in resistance causes a larger portion of the total system vacuum to fall across threshold valve 20, helping to keep it open at low vacuum levels.

Figure 4:
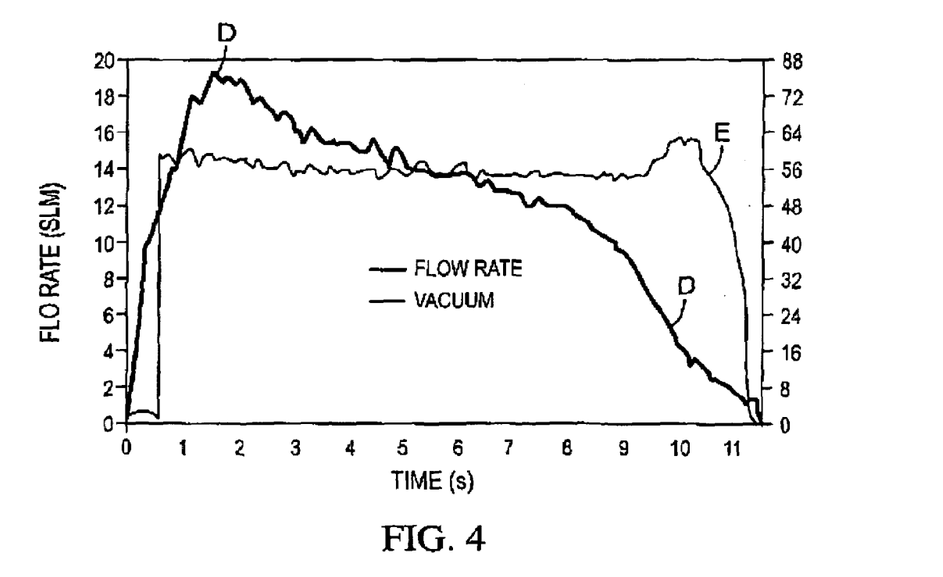
FIG. 4 is a graph illustrating one example of an inhalation through the device of FIG. 1.

As shown in FIG. 4, another benefit of the increased flow rate at low vacuum levels is that the user feels less resistance and may therefore comfortably finish the inhalation. In FIG. 4, line D represents the applied vacuum and line E represents the flow rate. As shown, line E increases low vacuum levels.

Figure 5:
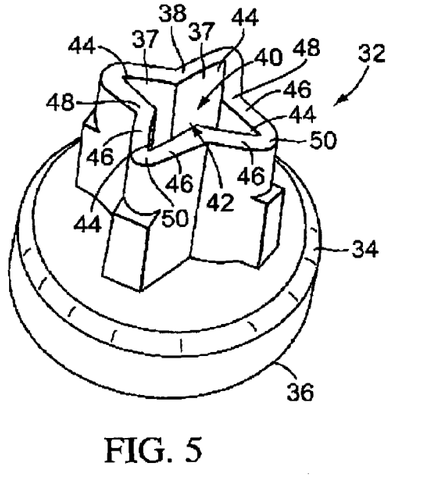
FIG. 5 is a top perspective view of one embodiment of a flow regulating valve according to the invention.
Figure 6:
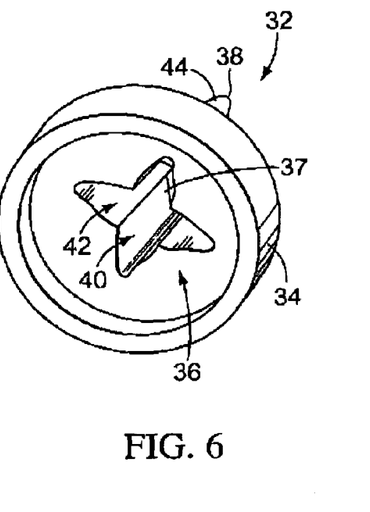
FIG. 6 is a bottom perspective view of the flow regulating valve of FIG. 5.

Referring now to FIGS. 5 and 6, one embodiment of a flow regulating valve 32 will be described. Valve 32 may be used in device 10 along with any of the other systems described herein. Valve 32 comprises a valve body 34 having an inlet end 36, an outlet end 38 and a gas flow passage 40 between the inlet end 36 and the outlet end 38. Valve body 34 is constructed of a resilient material, such as a silicone rubber. Valve body 34 at outlet end 38 has a central region 42 and a plurality of extending regions 44 that extend outwardly from central region 42. In operation, extending regions 44 are drawn together to limit the flow of gases through gas flow passage 40 as the vacuum level downstream of outlet end 38 increases.

As shown, each extending region 44 comprises a pair of walls 46 having a base end 48 and a top end 50, and the top ends 50 are connected at an acute angle. Each extending region 44 is connected to two adjacent extending regions 44 at the base ends 48 of the walls 46 to define the central region 42. In the arrangement of FIG. 5, the number of extending regions 44 is eight such that the two of the extending regions are perpendicular to the other two extending regions. However, it will be appreciated that other numbers of extending regions could also be used, such as two, three, five and the like.

When used in an aerosolization device, valve 32 may be used to increase flow resistance and thereby limit the flow rate to be within certain limits. At low vacuum levels, valve 32 remains fully open so that adequate flow rates may be achieved. At higher vacuum levels, extending regions 44 close to limit and eventually stop the flow through valve 32.

As best shown in FIG. 5, just beyond inlet end 36 is a boundary layer step 37 that is used to insure boundary layer separation for gases flowing through valve 32. This flow separation helps to insure a predictable pressure loss across valve 37. In this way, a predictable pressure loss is produced across a wide range of vacuums and flow rates.

Figure 7:
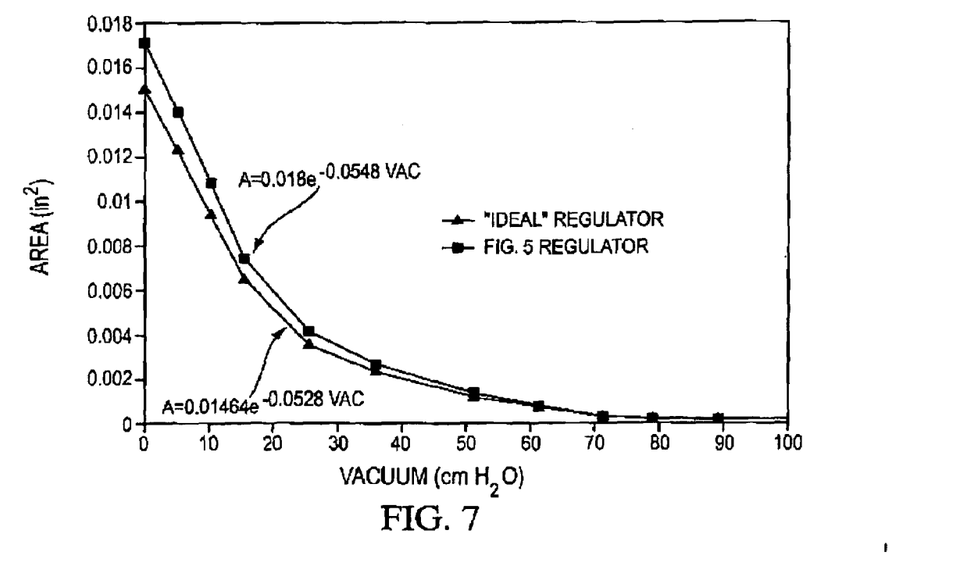
FIG. 7 is a graph illustrating the relationship between the applied load and the cross sectional area of the valve of FIGS. 5 and 6 when in a series-parallel architecture.

Valve 32 will find particular use in a series-parallel flow path arrangement, such as in device 10. Valve 32 is configured to be highly non-linear, i.e., the cross sectional area of central region 42 and extending regions 44 rapidly decrease as the vacuum increase. This is illustrated in FIG. 7 where the relationship between the cross sectional area and the applied vacuum is non-linear. Closing of valve 32 in this manner counteracts the flow through the parallel flow path so that the total flow through the system remains generally constant.

In a series-parallel architecture as shown in FIG. 1, an "ideal" flow regulating valve would produce a constant flow rate over a wide range of vacuum levels, including at the lowest possible levels where flow is permitted. For example, if receptacle 28 has a constant flow resistance, the parallel flow path having receptacle 28 has a constant flow resistance of $R_r$, $$R_r = 0.65 \sqrt{cmH_2O}/SLM.$$

The "ideal" flow regulating valve may be defined in terms of orifice area A versus locally applied vacuum (VAC) where $$A = 0.014638 e^{-0.0528\ VAC}.$$

This relationship is illustrated in FIG. 7

FIG. 7 also illustrates that the actual functioning of flow regulating valve 26 departs from that of the "ideal" valve. Instead valve 26 provides an increased flow at low vacuum levels to provide the benefits previously described.

Figure 8:
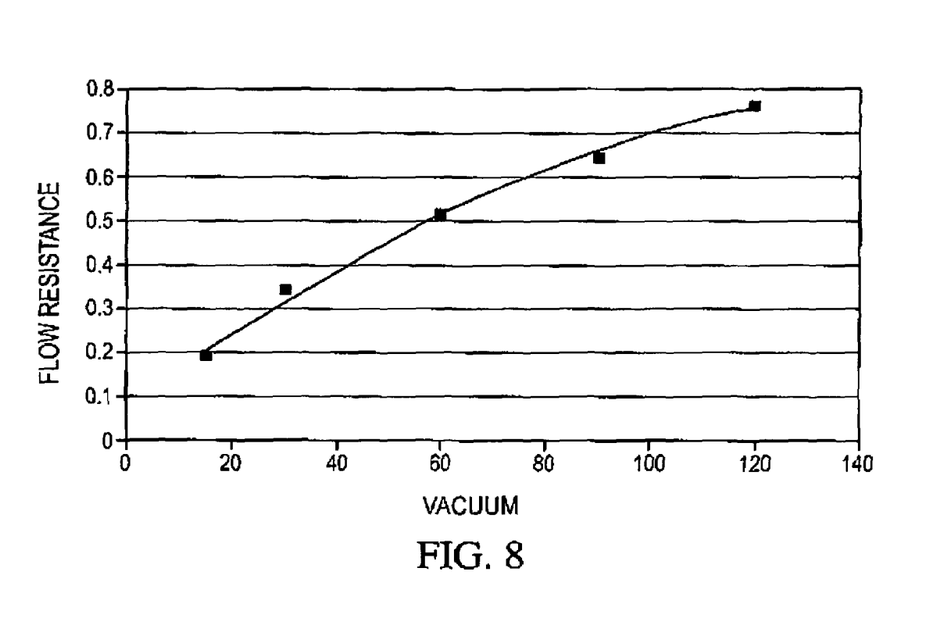
FIG. 8 is a graph illustrating the relationship between flow resistance and vacuum for the valve of FIG. 5 when in a series architecture.
Figure 9:
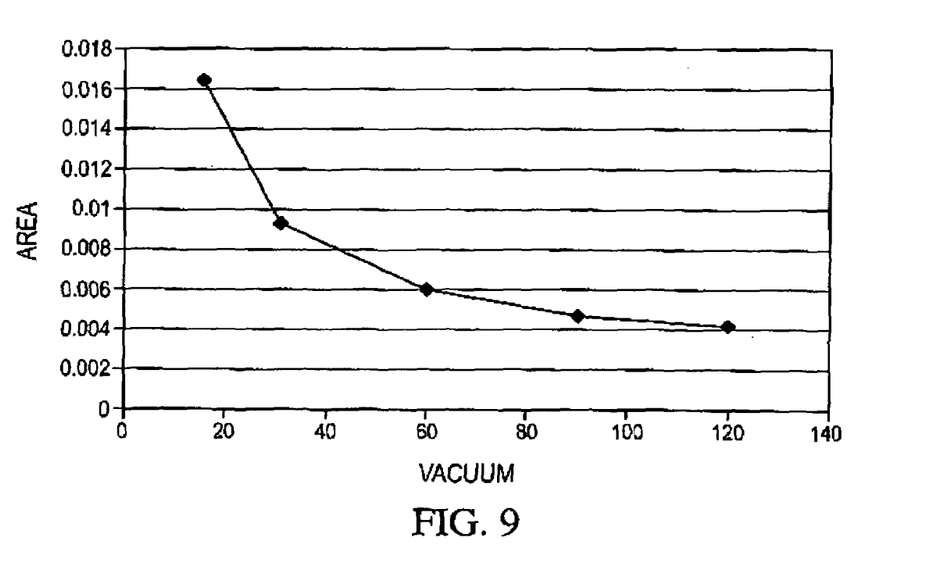
FIG. 9 is a graph illustrating the cross sectional area versus vacuum of the valve of FIG. 5 when in a series architecture.

As previously mentioned, when flow regulating valve 26 is followed by receptacle, a series architecture is provided. As such, flow regulating valve 26 is configured to function in a different manner. More specifically, valve 26 may be configured to produce a flow resistance versus vacuum curve as illustrated in FIG. 8. Accordingly, the cross sectional area versus vacuum curve for valve 26 is illustrated in FIG. 9. The curve in FIG. 9 (for the series arrangement) is much shallower that the curve of FIG. 7 (for the series-parallel arrangement).

The invention has now been described in detail for purposes of clarity of understanding. However, it will be appreciated that certain changes and modifications may be practiced within the scope of the appended claims.

What is claimed is:

1. A method for regulating air flow, the method comprising:
   providing a flow path arrangement having a flow regulating valve and a threshold valve, wherein the threshold valve is configured to open at a first vacuum level and to close at a second vacuum level that is less than the first vacuum level;
   producing a vacuum within the flow path arrangement sufficient to open the threshold valve and to permit a gas to exit the flow path arrangement at a certain flow rate; and
   maintaining the vacuum above the second vacuum level for at least a certain time to maintain the threshold valve open, with the flow regulating valve regulating the flow rate to be within a certain range while the threshold valve remains open,
   wherein the first vacuum level is in the range from about 20 cm $H_2O$ to about 50 cm $H_2O$, and wherein the second vacuum level is in the range from about 0 cm $H_2O$ to about 12 cm $H_2O$.

2. A method as in claim 1, wherein the flow path arrangement has a first flow path that divides into a second flow path and a third flow path, wherein the threshold valve is in the first flow path, the flow regulating valve is in the second flow path, and the powder is coupled to the third flow path.

3. A method as in claim 1, wherein the second vacuum level is less than about 8 cm $H_2O$.

4. A method as in claim 1, wherein the certain flow rate range is about 12 liters/min to about 16 liters/min for vacuums of about 15 cm $H_2O$ to about 80 cm $H_2O$.

5. A method as in claim 1, wherein the flow regulating valve comprises at least one deformable wall and an opposing surface, wherein the deformable wall moves toward the opposing surface as the vacuum downstream of the flow regulating valve increases to regulate the flow rate.

6. A method as in claim 1, wherein the flow regulating valve comprises a valve body having an inlet end, an outlet end and a gas flow passage between the inlet end and the outlet end, wherein the valve body is constructed of a resilient material and wherein the valve body at the outlet end has a central region and a plurality of extending regions that extend outwardly from the central region, and wherein the extending regions are drawn together to limit the flow of gases through the gas flow passage as the vacuum downstream of the outlet end increases.

7. A method for aerosolizing a powder, the method comprising:
   providing a flow path arrangement having a flow regulating valve and a threshold valve, wherein the threshold valve is configured to open at a first vacuum level and to close at a second vacuum level that is less than the first vacuum level;

providing an amount of powder that is in fluid communication with the flow path arrangement;

inhaling to produce a vacuum within the flow path arrangement sufficient to open the threshold valve and to permit a gas to exit the flow path arrangement at a certain flow rate; and continuing to inhale to maintain the vacuum above the second vacuum level for at least a certain time to maintain the threshold valve open and to aerosolize the powder, with the flow regulating valve regulating the flow rate to be within a certain range while the threshold valve remains open, wherein the first vacuum level is in the range from about 20 cm $H_2O$ to about 50 cm $H_2O$, and wherein the second vacuum level is in the range from about 0 cm $H_2O$ of about 12 cm $H_2O$.

8. A method as in claim 7, wherein the flow path arrangement has a first flow path that divides into a second flow path and a third flow path, wherein the threshold valve is in the first flow path, the flow regulating valve is in the second flow path, and the powder is coupled to the third flow path.

9. A method as in claim 7, wherein the second vacuum level is less than about 8 cm $H_2O$.

10. A method as in claim 7, wherein the flow path arrangement is coupled to a mouthpiece, and further wherein the inhaling step comprising inhaling through the mouthpiece.

11. A method as in claim 7, wherein the certain flow rate range is about 12 liters/min to about 16 liters/min for vacuums of about 15 cm $H_2O$ to about 80 cm $H_2O$.

12. A method as in claim 7, wherein the flow regulating valve comprises at least one deformable wall and an opposing surface, wherein the deformable wall moves toward the opposing surface as the vacuum downstream of the flow regulating valve increases to regulate the flow rate.

13. A method as in claim 12, wherein the flow regulating valve comprises a valve body having an inlet end, an outlet end-and a gas flow passage between the inlet end and the outlet end, wherein the valve body is constructed of a resilient material and wherein the valve body at the outlet end has a central region and a plurality of extending regions that extend outwardly from the central region, and wherein the extending regions are drawn together to limit the flow of gases through the gas flow passage as the vacuum downstream of the outlet end increases.

14. A method as in claim 7, wherein the powder is contained within a receptacle, and wherein the gas flow through the flow path arrangement flows through the receptacle to extract and aerosolize the powder.

15. An aerosolization device, comprising:

a housing having a mouthpiece;

a flow path arrangement in fluid communication with the mouthpiece, the flow path arrangement having a flow regulating valve and a threshold valve, wherein the threshold valve is configured to open at a first vacuum level and to close at a second vacuum level that is less than the first vacuum level; and wherein the housing includes a region that is adapted to hold a powder in fluid communication with the flow path arrangement, wherein air drawn through the mouthpiece opens the threshold valve once the first vacuum level is exceeded and remains open until the vacuum falls below the second vacuum level, and the flow rate of the air drawn through the mouthpiece is regulated by the flow regulating valve to remain within a certain range while the threshold valve remains open and wherein the first vacuum level is in the range from about 20 cm $H_2O$ to about 50 cm $H_2O$, and wherein the second vacuum level is in the range from about 0 cm $H_2O$ to about 12 cm $H_2O$.

16. A device as in claim 15, wherein the flow path arrangement has a first flow path that divides into a second flow path and a third flow path, wherein the threshold valve is in the first flow path, the flow regulating valve is in the second flow path, and the powder is coupled to the third flow path.

17. A device as in claim 16, wherein the second flow path and the third flow path combine to a fourth flow path that is connected to the mouthpiece.

18. A method as in claim 16, wherein the second vacuum level is less than about 8 cm $H_2O$.

19. A device as in claim 15, further comprising a receptacle that is held within the region, the receptacle having a chamber that is adapted to hold the powder.

20. A device as in claim 15, wherein the certain flow rate range is about 12 liters/min to about 16 liters/min for vacuums of about 15 cm $H_2O$ to about 80 cm $H_2O$.

21. A device as in claim 15, wherein the flow regulating valve comprises at least one deformable wall and an opposing surface, wherein the deformable wall moves toward the opposing surface as the vacuum downstream of the flow regulating valve increases to regulate the flow rate.

22. A device as in claim 15, wherein the flow regulating valve comprises a valve body having an inlet end, an outlet end and a gas flow passage between the inlet end and the outlet end, wherein the valve body is constructed of a resilient material and wherein the valve body at the outlet end has a central region and a plurality of extending regions that extend outwardly from the central region, whereby the extending regions are drawn together to limit the flow of gases through the gas flow passage as the vacuum downstream of the outlet end increases.

* * * * *